(12) United States Patent
Sandler et al.

(10) Patent No.: US 12,156,878 B1
(45) Date of Patent: Dec. 3, 2024

(54) COMPOSITIONS AND METHODS FOR MINIMIZING EFFECTS OF ALCOHOL INTOXICATION

(71) Applicant: SAFETY SHOT, INC., Jupiter, FL (US)

(72) Inventors: David Sandler, Lakewood, CO (US); Jarrett Boon, Phoenix, AZ (US); John Gulyas, Weston, FL (US); Gregory Blackman, Jensen Beach, FL (US)

(73) Assignee: SAFETY SHOT, INC., Jupiter, FL (US)

( * ) Notice: Subject to any disclaimer, the term of this patent is extended or adjusted under 35 U.S.C. 154(b) by 0 days.

(21) Appl. No.: 18/395,565

(22) Filed: Dec. 23, 2023

(51) Int. Cl.

| | |
|---|---|
| *A23L 2/52* | (2006.01) |
| *A61K 9/00* | (2006.01) |
| *A61K 31/137* | (2006.01) |
| *A61K 31/145* | (2006.01) |
| *A61K 31/194* | (2006.01) |
| *A61K 31/197* | (2006.01) |
| *A61K 31/198* | (2006.01) |
| *A61K 31/4415* | (2006.01) |
| *A61K 31/455* | (2006.01) |
| *A61K 31/4748* | (2006.01) |
| *A61K 31/51* | (2006.01) |
| *A61K 31/522* | (2006.01) |
| *A61K 31/525* | (2006.01) |
| *A61K 31/675* | (2006.01) |
| *A61K 31/7068* | (2006.01) |
| *A61K 31/714* | (2006.01) |
| *A61K 31/732* | (2006.01) |
| *A61K 36/258* | (2006.01) |
| *A61K 36/28* | (2006.01) |
| *A61K 36/288* | (2006.01) |
| *A61K 36/48* | (2006.01) |
| *A61K 47/02* | (2006.01) |
| *A61K 47/12* | (2006.01) |
| *A61P 25/32* | (2006.01) |

(52) U.S. Cl.
CPC .............. *A61K 31/522* (2013.01); *A23L 2/52* (2013.01); *A61K 9/0095* (2013.01); *A61K 31/137* (2013.01); *A61K 31/145* (2013.01); *A61K 31/194* (2013.01); *A61K 31/197* (2013.01); *A61K 31/198* (2013.01); *A61K 31/4415* (2013.01); *A61K 31/455* (2013.01); *A61K 31/4748* (2013.01); *A61K 31/51* (2013.01); *A61K 31/525* (2013.01); *A61K 31/675* (2013.01); *A61K 31/7068* (2013.01); *A61K 31/714* (2013.01); *A61K 31/732* (2013.01); *A61K 36/258* (2013.01); *A61K 36/28* (2013.01); *A61K 36/288* (2013.01); *A61K 36/48* (2013.01); *A61K 47/02* (2013.01); *A61K 47/12* (2013.01); *A61P 25/32* (2018.01)

(58) Field of Classification Search
None
See application file for complete search history.

(56) References Cited

U.S. PATENT DOCUMENTS

| | | | |
|---|---|---|---|
| 9,186,350 B2 | 11/2015 | Blackman | |
| 10,028,991 B2 | 7/2018 | Blackman | |
| 2015/0132280 A1* | 5/2015 | Lopez | ..................... A61P 25/24 |
| | | | 544/266 |
| 2021/0220422 A1* | 7/2021 | Parker | ................... A61K 36/28 |

FOREIGN PATENT DOCUMENTS

| | | | |
|---|---|---|---|
| CN | 1593395 A | * | 3/2005 |
| RU | 2605767 C2 | * | 12/2016 |

OTHER PUBLICATIONS

Blood Alcohol Concentration (BAC), The University of Texas at Austin, University Health Services, accessed on Feb. 27, 2024. (Year: 2024).*

Monagas et al., "Understanding Plant to Extract Ratios in Botanical Extracts," Frontiers in Pharmacology, vol. 13, No. 981978, 10 pages, (2022).

Mokhtari, V. et al., "A Review on Various Uses of N-Acetyl Cysteine," Cell Journal, vol. 19, No. 1, 7 pages, (2017).

* cited by examiner

*Primary Examiner* — Melissa S Mercier
(74) *Attorney, Agent, or Firm* — Hoxie & Associates LLC

(57) ABSTRACT

A composition includes a plurality of ingredients, which when combined, have the unexpected effect of accelerating the removal of alcohol from an individual as observed by breathalyzer. The removal occurs at a much faster rate than under normal physiological means. By administering the composition to an inebriated individual, the rate at which a person sobers up, occurs at a faster rate than would occur under normal physiological time frames. This same composition may also increase mental acuity in a person not suffering from alcohol intoxication.

29 Claims, No Drawings

COMPOSITIONS AND METHODS FOR MINIMIZING EFFECTS OF ALCOHOL INTOXICATION

FIELD OF THE DISCLOSURE

The invention relates a composition which reduces the levels of alcohol in an individual's system and/or increases mental acuity. The invention particularly relates to such a composition that reduces the levels of alcohol in an individual's system as observed by measurement by breathalyzer.

BACKGROUND OF THE DISCLOSURE

Alcohol is commonly used within a variety of beverage types. As a result of its status and ease of manufacture, it is one of the most widely used drugs in the world, acting as a central nervous system depressant. The central nervous system, therefore, is the body system that is most severely affected by alcohol. The drug quickly enters the bloodstream where, depending on the user, it can have numerous effects. Blood alcohol levels are used to legally define if an individual suffers from alcohol intoxication, or is considered "drunk." In most states, the blood alcohol legal limit usually falls between 0.08 and 0.10. The degree to which the central nervous system function is impaired is directly proportional to the concentration of alcohol in the blood.

The American Medical Association has defined the blood alcohol concentration (BAC) level of impairment for all people to be 0.04 grams/100 milliliters of blood (equivalent to 0.04 grains/210 liters of breath). Numerous studies have been undertaken in order to better understand the affects alcohol has on individuals, and how they are commonly expressed. For example, at BAC levels of 0.03 to 0.12, it is not uncommon for individuals to feel euphoria and have one or more symptoms: mild euphoria, become more social and talkative, increased self-confidence, decreased inhibitions, diminution of attention, judgment and control, sensory-motor impairment, and loss of efficiency in finer performance tests. At levels of 0.09-0.25. individuals begin to suffer from emotional instability, loss of critical judgments, impairment of perception, memory and comprehension, deceased sensatory response, increased reaction times, reduced visual acuity, impaired balance, lack of sensory-motor coordination, and drowsiness. At BAC of 0.18-0.3, individuals often become confused, disorientated, have mental confusion, dizziness and exaggerated emotional states, suffer from disturbances in vision and perception, have increased pain thresholds, suffer from apathy, and have slurred speech. At levels of 0.25-0.4, individuals may suffer from near complete loss of motor functions, decreased responses to stimuli, lack of muscular coordination; and impaired consciousness. At levels greater than 0.45, complete unconsciousness and death from respiratory arrest could result.

Once alcohol is consumed, the body handles the drug through the processes of absorption, distribution, and elimination. All three processes generally occur simultaneously. Alcohol is absorbed from the stomach and small intestine by diffusion. Most absorption occurs from the small intestine due to its large surface area and rich blood supply. The rate of absorption varies with the emptying time of the stomach. Generally, the higher the alcohol concentration of the beverage, the faster the rate of absorption.

Alcohol is eliminated from the body by excretion and metabolism, typically through elimination by the kidney (urine), lung (exhale), or liver where it is chemically broken down to acetic acid. A small portion of alcohol is excreted, such as through the breath, leaving the body as alcohol, unchanged.

Mental acuity comprises a person's ability to reason, focus, and recall information at optimum speeds. Losing mental acuity, or sharpness of the mind, is often referred to as cognitive decline and often occurs as a natural aspect of aging.

What is needed in the art, therefore, is a composition, which when taken by individuals suffering from alcohol intoxication, results in the clearance of alcohol from the body at a faster rate than clearance associated under normal physiology. It would also be desirable in the art to have a composition which can improve or increase mental acuity, especially in those who have lost such acuity due to aging.

SUMMARY OF THE DISCLOSURE

In one aspect, the disclosure provides a Composition [Composition1] for reducing blood alcohol concentrations (BAC) in an individual in need thereof, for example where the individual is impaired or suspected of being impaired by an alcohol, comprising administering an effective amount of:
  theacrine;
  methylliberine;
  theobromine;
  caffeine;
  cdp choline;
  synephrine;
  *Macuna pruriens;*
  apple pectin;
  dandelion extract;
  n-acetyl cysteine; and
  milk thistle;
  and optionally *Ginseng*, for example Korean Red *Ginseng* (aka *Panax ginseng*/Asian *Ginseng*) and derivations thereof that include extracted ginsenosides; whereby the administration of the composition to the individual results in clearance of alcohol from the body at a faster rate than clearance associated observed under normal physiological conditions; for example, as measured by a standard breathalyzer machine.

In a further aspect, the present disclosure provides a Composition [Composition 2] for improving cognitive performance in an individual impaired or suspected of being impaired by an alcohol comprising an effective amount of:
  theacrine;
  methylliberine;
  theobromine;
  caffeine;
  cdp choline;
  synephrine;
  *Macuna pruriens;*
  apple pectin;
  dandelion extract;
  n-acetyl cysteine; and
  milk thistle;
  and optionally *Ginseng*, for example Korean Red *Ginseng* (aka *Panax ginseng*/Asian *Ginseng*) and derivations thereof that include extracted ginsenosides;
  wherein introducing the composition into the individual improves cognitive performance.

In a further aspect, the present disclosure provides a Method [Method 1] for reducing blood alcohol concentrations in an individual in need thereof, the method comprising i) providing to the individual a composition according to any of Compositions of the present disclosure. In some embodiments, the present methods further comprise the step of: ii) administering the composition to the individual; whereby the administration of the composition results in either: a) the clearance of alcohol from the body at a faster rate than clearance associated with, or observed under normal physiology; or b) the improvement of cognitive ability at a faster rate than improvement associated with, or observed under normal physiology.

In a further aspect, the present disclosure provides a Method [Method 2] for improving cognitive ability in an individual in need thereof who is suffering from, or is suspected of suffering from, cognitive impairment due to alcohol, comprising providing to the individual a composition according to any of Compositions of the present disclosure. In some embodiments, the Method further comprises the step of: ii) administering the composition to the individual; whereby the administration of the composition results in the improvement of cognitive ability; for example at a faster rate than improvement associated with, or observed under normal physiology.

In a further aspect, the present disclosure provides a Method [Method 3] for improving cognitive ability (and/or mental acuity) in an individual not suffering from alcohol intoxication, comprising: i) providing to the individual a composition according to any of Compositions 1 and 1.1 et seq., and/or Compositions 2 and 2.1 et seq. In some embodiments, the Method further comprises the step of ii) administering the composition to the individual; whereby the administration of the composition results in the improvement of cognitive ability and/or mental acuity.

In a further aspect, the present disclosure provides a Method [Method 4] for reducing, alleviating or ameliorating the severity of symptoms associated with alcohol intoxication (e.g., symptoms associated with "hangover"), including for example and not limitation, headache, nausea and fatigue, comprising: i) providing to the individual a composition according to any of Compositions 1 and 1.1 et seq., and/or Compositions 2 and 2.1 et seq. In some embodiments, the Method further comprises the step of ii) administering the composition to the individual; whereby the administration of the composition results in the reducing, alleviating or ameliorating the severity of symptoms associated with alcohol intoxication.

DETAILED DESCRIPTION

Unless otherwise specified, all percentages and amounts expressed herein and elsewhere in the specification should be understood to refer to percentages by weight.

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

An "individual" refers to a human being. In some embodiments, the individual is an adult human; i.e., a human of age 17 or older.

The terms "administering" and "applying to the individual" as used in connection with the methods of the present disclosure is intended to mean introducing a Composition as described herein into the oral cavity of an individual, for example, by the individual, a first responder, or a physician, a physical therapist or other appropriate health care provider.

Unless otherwise indicated, amounts of ingredients are provided as mg dry powder weight per single serving. A serving can be in the form of a tablet, capsule, caplet, pill, gel cap, dry powder, liquid, or suspension. In some embodiments, servings are provided as a liquid solution or suspension. In some embodiments, the liquid solution or suspension is provided in a container used for consumer beverages, for example, in a can or bottle. In some embodiments, single servings of the compositions of the present disclosure are provided in 12 oz cans or bottles.

Unless otherwise indicated, the term "about," when used in reference to a range of values, should be understood to refer to +/−10% of the recited value(s). As used throughout, ranges are used as shorthand for describing each and every value that is within the range. Any value within the range can be selected as the terminus of the range.

The compositions of the present disclosure can include one or more preservatives. The preservatives can be selected from any preservative known to be suitable for use in liquid beverages and liquid pharmaceutical formulations. Suitable preservatives include benzoates, including sodium Benzoate, and sorbates such as potassium sorbate. Also useful are butylated hydroxytoluene (BHT) and BHT derivatives, and herbal extracts and essential oils, and acids. The preservatives can be present in the present compositions in amounts of from about 0.01% to about 3% w/v, most typically from about 0.01% to about 1%, w/v; or 0.1%-0.2% w/v. In some embodiments, the preservatives are present in an amount of about 80 to about 200 mg/serving each.

The compositions of the present disclosure can include antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, dithiocarbamates, citric acid, tartaric acid, and malic acid. The preservatives can be present in the present compositions in amounts of from about 0.01% to about 3% w/v, most typically from about 0.01% to about 1%, w/v; or 0.1%-0.2% w/v.

The compositions of the present disclosure can include a flavor component, that can include one or more flavorants, or flavors. As used herein, the terms "flavor" or "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, *eucalyptus*, thyme oil, cedar leave oil, oil of nutmeg, oil of sage, oil of bitter almonds and *cassia* oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available strawberry, orange, grape, cherry, vanilla, mint and citrus flavors, ethyl maltol, vanillin, and mixtures thereof, as well as masking agents such as sodium gluconate, sodium citrate, disodium phosphate, sodium chloride, potassium chloride, dipotassium phosphate as masking agents, acetic acid, caramel, ginger and licorice. The amount of flavoring and/or masking agent may depend on a number of factors, including the organoleptic effect desired. Flavors will be present in any amount as desired by those of ordinary skill in the art.

The compositions of the present disclosure can include a sweetener component, which can include one or more sweeteners. As used herein, the term "sweetener" is intended to mean a compound used to impart sweetness to a preparation. Such compounds include, by way of example and without limitation, aspartame, polyols such as mannitol, sorbitol and xylitol, acesulfame, neotame, *stevia*, dextrose, saccharin sodium, fructose, high fructose corn syrup, maltodextrin, sucralose, sucrose, monk fruit and other materials known to one of ordinary skill in the art, and combinations thereof. In some embodiments, the sweetener is present in an amount of about 350 to about 450 mg/serving each, or in aggregate.

The compositions of the present disclosure can include one or more colorants. As used herein, the term "colorant" refers to pigments and/or dyes or a combination thereof, that are used to impart color to the composition. In some embodiments, colorants include, but are not limited to, FD&C approved colorants. Examples include caramel colorant, red colorant Enocianin, Indigo yellow, Quinoline yellow, Quinizarine Green, FD&C Blue #1 Aluminum Lake, FD&C Blue #2, other FD&C Blue colors, titanium dioxide, iron oxide, and natural colors that would come from, for example, beet, radish (purple and red), *spirulina* (green and blue), beta carotene, turmeric, etc., and/or combinations thereof.

In some embodiments, the composition comprises stabilizers, which may include preservatives such as but not limited to benzaldehydes, PEG (poly ethyl glycohol), or carboxylic acid. In still other embodiments, the Composition may be prepared using emulsifiers or suspension agents. Surfactants and buffers may also be employed with the Compositions of the application.

The present compositions are typically prepared as solutions or suspensions for oral administration; i.e., by ingestion through the mouth, for example by drinking. Oral administration also is intended to include administering through devices that are designed to deliver components to the stomach, for example a feeding tube or nasal gastric tube.

In some embodiments, the compositions of the present disclosure are provided in sealed containers, for example beverage cans, for consumption by the individual in need thereof.

The pharmaceutical compositions provided herein contain therapeutically effective amounts of one or more of compounds provided herein that are useful in the treating, reducing, resolving, eliminating, ameliorating and/or preventing the conditions described herein, or one or more of the symptoms thereof. In particular, administration of the present compositions to an individual suffering from an undesirably elevated blood alcohol level (undesirably elevated BAC) results in increased rates of reduction of blood alcohol concentration (i.e. increased rate of lowering of BAC) compared to the rate associated with, or observed under normal physiology.

In a first aspect, the present disclosure provides a Composition [Composition1] for reducing blood alcohol concentrations (BAC) in an individual impaired or suspected of being impaired by an alcohol comprising administering an effective amount of:
   theacrine;
   methylliberine;
   theobromine;
   caffeine;
   cdp choline;
   synephrine;
   *Macuna pruriens*;
   apple pectin;
   dandelion extract;
   n-acetyl cysteine; and
   milk thistle;
   and optionally *Ginseng*, for example Korean Red *Ginseng* (aka *Panax ginseng*/Asian *Ginseng*) and/or derivations thereof that include extracted ginsenosides;
whereby the administration of the composition to the individual results in clearance of alcohol from the body at a faster rate than clearance associated with, or observed, under normal physiological conditions; for example as measured by a standard breathalyzer machine.

The present disclosure further provides the following embodiments of Composition 1:
   1.1 Composition 1, comprising at least one B vitamin selected from the group consisting of B1 (Thiamine), B2 (Riboflavin), B3 (Niacin), B5 (Pantothenic Acid), B6 (pyridoxine; Pyridoxal 5 Phosphate and Pyridoxine HCL), B12 (methylcobalamin), and combinations thereof.
   1.2 Composition 1 or 1.1, further comprising n-acetyl tyrosine.
   1.3 Any preceding Composition 1 or 1.1 et seq., further comprising taurine.
   1.4 Any preceding Composition 1 or 1.1 et seq., further comprising cocoa extract.
   1.5 Any preceding Composition 1 or 1.1 et seq., further comprising phenylalanine.
   1.6 Any preceding Composition 1 or 1.1 et seq., further comprising huperzine A.
   1.7 Any preceding Composition 1 or 1.1 et seq., further comprising magnesium citrate.
   1.8 Any preceding Composition 1 or 1.1 et seq., further comprising potassium chloride.
   1.9 Any preceding Composition 1 or 1.1 et seq., further comprising sodium citrate.
   1.10 Any preceding Composition 1 or 1.1 et seq., further comprising calcium citrate.
   1.11 Any preceding Composition 1 or 1.1 et seq., further comprising quercetin.
   1.12 Any preceding Composition 1 or 1.1 et seq., further comprising hordenine.
   1.13 Any preceding Composition 1 or 1.1 et seq., further comprising *Eria jarensis*.
   1.14 Any preceding Composition 1 or 1.1 et seq., further comprising glycine.
   1.15 Any preceding Composition 1 or 1.1 et seq., further comprising further comprising one or more members selected from the group consisting of palmitoylethanolamide, artichoke extract, yellow dock root (*Rumex crispus*), turmeric, glutathione, ginger, licorice, chitosan, inulin, and combinations thereof
   1.16 Any preceding Composition 1 or 1.1 et seq., further comprising one or more of the following components: betaine (Anhydrous or HCL); Green Tea Extract (higher EGCG); Chinese Lacquer Plant (*Toxicodendron verniciflum*); Licorice Root; Alpha Lipoic Acid; Probiotics (e.g., *Lactobacillus* and *Bifidobacterium*); Japanese Mountain Ash (*Sorbus commixta*); Japanese Alder (*Alnus japonica*); and/or Asian Hazel (*Corylus heterophylla*).
   1.17 Any preceding Composition 1 or 1.1 et seq., further comprising water wherein the water is present at a concentration of from about 80 weight percent to 99 weight percent.
   1.18 Any preceding Composition 1 or 1.1 et seq., wherein the water is present at a concentration of from about 85 weight percent to 98 weight percent.

1.19 Composition 1.18, wherein the water is present at a concentration of from about 90 weight percent to 97 weight percent.

1.20 Any preceding Composition 1 or 1.1 et seq., wherein the composition contains the following components (each amount should be read as about that amount):

TABLE 1

| Component | Mg/serving |
|---|---|
| theacrine | about 5 to about 150 |
| methylliberine | about 5 to about 120 |
| theobromine | about 50 to about 250 |
| caffeine | about 50 to about 400 |
| cdp choline | about 25 to about 500 |
| synephrine (or synephrine HCl) | about 10 to about 150 |
| macuna pruriens | about 50 to about 500 |
| apple pectin | about 500 to about 3000 |
| dandelion extract | about 50 to about1000 |
| N-acetyl cysteine | about 100 to about 1500 |
| milk thistle | about 50 to about 600 |
| (Optionally) Ginseng, for example Korean Red Ginseng (aka Panax Ginseng/Asian Ginseng) and/or derivations thereof that include extracted ginsenosides | about 25 to about 400 |

1.21 Composition 1.21, further comprising one or more of the following components (each amount should be read as about that amount):

TABLE 2

| Component | Mg/serving |
|---|---|
| B Vitamin; e.g. one or more of B1 (Thiamine), B2 (Riboflavin), B3 (Niacin), B5 (Pantothenic Acid), B6 (pyridoxine; Pyridoxal 5 Phosphate and Pyridoxine HCL), B12 (methylcobalamin) | about 9 to about 171 |
| N-acetyl tyrosine | about 100 to about 1000 |
| Taurine | about 100 to about1000 |
| Cocoa extract | about 100 to about 1000 |
| Phenylalanine | about 50 to about 300 |
| Huperzine A | about 5 to about 100 |
| Magnesium citrate | about 50 to about 800 |
| Potassium chloride | about 25 to about 500 |
| Sodium citrate | about 100 to about 1500 |
| Calcium citrate | about 50 to about 1000 |
| Citric acid | about 50 to about 1500 |
| Quercetin | about 50 to about 500 |
| Hordenine | about 5 to about 150 |
| Eria jarensis | about 50 to about 750 |
| Glycine | about 50 to about 500 |

1.22 Composition 1.21, wherein the composition comprises 1, 2, 3, 4, 5, 6, 7, 8, 9, 10, 11, 12, 13 or all 14 of the recited components of Table 2.

1.23 Composition 1.22, wherein the composition does not contain one of more of Quercetin, Hordenine and/or *Eria jarensis*.

1.24 Any preceding Composition 1 or 1.1 et seq., further comprising one or more of the following components (each amount should be read as about that amount):

TABLE 3

| Component | Mg/serving |
|---|---|
| Betaine (Anhydrous or HCL) | about 500 to about 3000 |
| Green Tea Extract (higher EGCG) | about 50 to about 500 |
| Chinese Lacquer Plant (*Toxicodendron vernicifluum*) | about 50 to about 500 |
| Licorice Root | about 50 to about 500 |
| Alpha Lipoic Acid | about 100 to about 1000 |
| Probiotics (e.g., *Lactobacillus* and *Bifidobacterium*) | about 5 to about 250 |
| Japanese Mountain Ash (*Sorbus Commixta*) | about 25 to about 500 |
| Japanese Alder (*Alnus Japonica*) | about 25 to about 500 |
| Asian Hazel (*Corylus Heterophylla*). | about 25 to about 500 |

1.25 Composition 1.24, 1.21, wherein the composition comprises 1, 2, 3, 4, 5, 6, 7, 8 or all 9 of the recited components of Table 3.

1.26 Any preceding Composition 1 or 1.1 et seq., wherein the composition further comprises a member of the group consisting of palmitoylethanolamide, artichoke extract, yellow dock root (*Rumex crispus*), turmeric, glutathione, ginger, licorice, chitosan, inulin, and combinations thereof.

1.27 Any preceding Composition 1 or 1.1 et seq., wherein alcohol is cleared from the body at a faster rate that is at least 10% faster than clearance associated with, or observed, under or associated with normal physiological conditions.

1.28 Any preceding Composition 1 or 1.1 et seq., wherein alcohol is cleared from the body at a faster rate that is at least 15% faster than clearance observed under or associated with normal physiological conditions.

1.29 Any preceding Composition 1 or 1.1 et seq., wherein alcohol is cleared from the body at a faster rate that is at least 20% faster than clearance observed under or associated with normal physiological conditions.

1.30 Any preceding Composition 1 or 1.1 et seq., wherein alcohol is cleared from the body at a faster rate that is at least 25% faster than clearance observed under or associated with normal physiological conditions.

1.31 Any preceding Composition 1 or 1.1 et seq., wherein alcohol is cleared from the body at a faster rate that is at least 30% faster than clearance observed under or associated with normal physiological conditions.

1.32 Any preceding Composition 1 or 1.1 et seq., wherein the BAC of the individual is decreased by greater than 20 mg % per hour after administration of the composition.

1.33 Any preceding Composition 1 or 1.1 et seq., wherein the BAC of the individual is decreased by greater than 21 mg % per hour after administration of the composition.

1.34 Any preceding Composition 1 or 1.1 et seq., wherein the BAC of the individual is decreased by greater than 22 mg % per hour after administration of the composition.

1.35 Any preceding Composition 1 or 1.1 et seq., wherein the BAC of the individual is decreased by greater than 23 mg % per hour after administration of the composition.

1.36 Any preceding Composition 1 or 1.1 et seq., wherein the BAC of the individual is decreased by greater than 24 mg % per hour after administration of the composition.

1.37 Any preceding Composition 1 or 1.1 et seq., wherein the BAC of the individual is decreased by greater than 25 mg % per hour after administration of the composition.

1.38 Any preceding Composition 1 or 1.1 et seq., wherein the composition is a liquid for oral administration.

1.39 Any preceding Composition 1 or 1.1 et seq., wherein the composition is in the form of a tablet, capsule, caplet, pill, gel cap, dry powder, liquid, or suspension.

In a further aspect, the present disclosure provides a Composition [Composition 2] for improving cognitive performance in an individual impaired or suspected of being impaired by an alcohol comprising an effective amount of:

theacrine;
methylliberine;
theobromine;
caffeine;
cdp choline;
synephrine;
*Macuna pruriens;*
apple pectin;
dandelion extract;
n-acetyl cysteine; and
milk thistle;
and optionally *Ginseng*, for example Korean Red *Ginseng* (aka *Panax Ginseng*/Asian *Ginseng*) and/or derivations thereof that include extracted ginsenosides;
wherein introducing the composition into the individual improves cognitive performance.

The present disclosure further provides the following embodiments of Composition 2:

2.1 Composition 2, comprising at least one B vitamin selected from the group consisting of B1 (Thiamine), B2 (Riboflavin), B3 (Niacin), B5 (Pantothenic Acid), B6 (pyridoxine), B12 (methylcobalamin), and combinations thereof.

2.2 Composition 2 or 2.1, further comprising n-acetyl tyrosine.

2.3 Any preceding Composition 2 or 2.1 et seq., further comprising taurine.

2.4 Any preceding Composition 2 or 2.1 et seq., further comprising cocoa extract.

2.5 Any preceding Composition 2 or 2.1 et seq., further comprising phenylalanine.

2.6 Any preceding Composition 2 or 2.1 et seq., further comprising huperzine A.

2.7 Any preceding Composition 2 or 2.1 et seq., further comprising magnesium citrate.

2.8 Any preceding Composition 2 or 2.1 et seq., further comprising potassium chloride.

2.9 Any preceding Composition 2 or 2.1 et seq., further comprising sodium citrate.

2.10 Any preceding Composition 2 or 2.1 et seq., further comprising calcium citrate.

2.11 Any preceding Composition 2 or 2.1 et seq., further comprising quercetin.

2.12 Any preceding Composition 2 or 2.1 et seq., further comprising hordenine.

2.13 Any preceding Composition 2 or 2.1 et seq., further comprising *Eria jarensis*.

2.14 Any preceding Composition 2 or 2.1 et seq., further comprising glycine.

2.15 Any preceding Composition 2 or 2.1 et seq., further comprising further comprising one or more members selected from the group consisting of palmitoylethanolamide, artichoke extract, yellow dock root (*Rumex crispus*), turmeric, glutathione, ginger, licorice, chitosan, inulin, and combinations thereof 2.16 Any preceding Composition 2 or 2.1 et seq., further comprising one or more of the following components: betaine (Anhydrous or HCL); Green Tea Extract (higher EGCG); Chinese Lacquer Plant (*Toxicodendron vernicifluum*); Licorice Root; Alpha Lipoic Acid; Probiotics (e.g., *Lactobacillus* and *Bifidobacterium*); Japanese Mountain Ash (*Sorbus commixta*; Japanese Alder (*Alnus Japonica*); and/or Asian Hazel (*Corylus Heterophylla*).

2.17 Any preceding Composition 2 or 2.1 et seq., further comprising water wherein the water is present at a concentration of from about 80 weight percent to 99 weight percent.

2.18 Composition 2.18, wherein the water is present at a concentration of from about 85 weight percent to 98 weight percent.

2.19 Composition 2.18, wherein the water is present at a concentration of from about 90 weight percent to 97 weight percent.

2.20 Any preceding Composition 2 or 2.1 et seq., wherein the composition contains the following components (each amount should be read as about that amount):

TABLE 4

| Component | mg/serving |
| --- | --- |
| theacrine | about 5 to about 150 |
| methylliberine | about 5 to about 120 |
| theobromine | about 50 to about 250 |
| caffeine | about 50 to about 400 |
| cdp choline | about 25 to about 500 |
| synephrine (or synephrine HCl) | about 10 to about 150 |
| macuna pruriens | about 50 to about 500 |
| apple pectin | about 500 to about 3000 |
| dandelion extract | about 50 to about1000 |
| N-acetyl cysteine | about 100 to about 1500 |
| milk thistle | about 50 to about 600 |
| (Optionally) Ginseng, for example Korean Red Ginseng (aka Panax Ginseng/Asian Ginseng) and/or derivations thereof that include extracted ginsenosides | about 25 to about 400 |

2.21 Composition 2.20, further comprising one or more of the following components (each amount should be read as about that amount):

TABLE 5

| Component | Mg/Serving |
| --- | --- |
| B Vitamin; e.g. one or more of B1, (Thiamine), B2 (Riboflavin), B3 (Niacin), B5 (Pantothenic Acid), B6 (pyridoxine; Pyridoxal 5 Phosphate and Pyridoxine HCL), B12 (methylcobalamin) | about 9 to about 171 |
| N-acetyl tyrosine | about 100 to about 1000 |
| Taurine | about 100 to about1000 |
| Cocoa extract | about 100 to about 1000 |
| Phenylalanine | about 50 to about 300 |

TABLE 5-continued

| Component | Mg/Serving |
| --- | --- |
| Huperzine A | about 5 to about 100 |
| Magnesium citrate | about 50 to about 800 |
| Potassium chloride | about 25 to about 500 |
| Sodium citrate | about 100 to about 1500 |
| Calcium citrate | about 50 to about 1000 |
| Citric acid | about 50 to about 1500 |
| Quercetin | about 50 to about 500 |
| Hordenine | about 5 to about 150 |
| Eria jarensis | about 50 to about 750 |
| Glycine | about 50 to about 500 |

2.22 Composition 2.22, wherein the composition comprises 1, 2, 3, 4, 5, 6, 7, 8, 9, 10, 11, 12, 13 or all 14 of the recited components of Table 5.

2.23 Composition 2.22, wherein the composition does not contain one of more of Quercetin, Hordenine and/or *Eria jarensis*.

2.24 Any preceding Composition 2 or 2.1 et seq., further comprising one or more of the following components (each amount should be read as about that amount):

TABLE 6

| Component | Mg/serving |
| --- | --- |
| Betaine (Anhydrous or HCL) | about 500 to about 3000 |
| Green Tea Extract (higher EGCG) | about 50 to about 500 |
| Chinese Lacquer Plant (*Toxicodendron vernicifluum*) | about 50 to about 500 |
| Licorice Root | about 50 to about 500 |
| Alpha Lipoic Acid | about 100 to about 1000 |
| Probiotics (e.g., Lactobacillus and Bifidobacterium) | about 5 to about 250 |
| Japanese Mountain Ash (*Sorbus Commixta*) | about 25 to about 500 |
| Japanese Alder (*Alnus Japonica*) | about 25 to about 500 |
| Asian Hazel (*Corylus Heterophylla*). | about 25 to about 500 |

2.25 Composition 2.24, wherein the composition comprises 1, 2, 3, 4, 5, 6, 7, 8 or all 9 of the recited components of Table 6.

2.26 Any preceding Composition 2 or 2.1 et seq., wherein the composition further comprises a member of the group consisting of palmitoylethanolamide, artichoke extract, yellow dock root (*Rumex crispus*), turmeric, glutathione, ginger, licorice, chitosan, inulin, and combinations thereof.

2.27 Any preceding Composition 2 or 2.1 et seq., wherein alcohol is cleared from the body at a faster rate that is at least 10% faster than clearance observed under or associated with normal physiological conditions.

2.28 Any preceding Composition 2 or 2.1 et seq., wherein alcohol is cleared from the body at a faster rate that is at least 15% faster than clearance observed under or associated with normal physiological conditions.

2.29 Any preceding Composition 2 or 2.1 et seq., wherein alcohol is cleared from the body at a faster rate that is at least 20% faster than clearance observed under or associated with normal physiological conditions.

2.30 Any preceding Composition 2 or 2.1 et seq., wherein alcohol is cleared from the body at a faster rate that is at least 25% faster than clearance observed under or associated with normal physiological conditions.

2.31 Any preceding Composition 2 or 2.1 et seq., wherein alcohol is cleared from the body at a faster rate that is at least 30% faster than clearance observed under or associated with normal physiological conditions.

2.32 Any preceding Composition 2 or 2.1 et seq., wherein the BAC of the individual is decreased by greater than 20 mg % per hour after administration of the composition.

2.33 Any preceding Composition 2 or 2.1 et seq., wherein the BAC of the individual is decreased by greater than 21 mg % per hour after administration of the composition.

2.34 Any preceding Composition 2 or 2.1 et seq., wherein the BAC of the individual is decreased by greater than 22 mg % per hour after administration of the composition.

2.35 Any preceding Composition 2 or 2.1 et seq., wherein the BAC of the individual is decreased by greater than 23 mg % per hour after administration of the composition.

2.36 Any preceding Composition 2 or 2.1 et seq., wherein the BAC of the individual is decreased by greater than 24 mg % per hour after administration of the composition.

2.37 Any preceding Composition 2 or 2.1 et seq., wherein the BAC of the individual is decreased by greater than 25 mg % per hour after administration of the composition.

2.38 Any preceding Composition 2 or 2.1 et seq., wherein the composition is a liquid for oral administration.

2.39 Any preceding Composition 2 or 2.1 et seq., wherein the composition is in the form of a tablet, capsule, caplet, pill, gel cap, dry powder, liquid, or suspension.

In a further aspect, the present disclosure provides a Method [Method 1] for reducing blood alcohol concentrations in an individual in need thereof, the method comprising:

i) providing to the individual a composition according to any of Compositions 1 and 1.1 et seq., and/or Compositions 2 and 2.1 et seq.

The present disclosure further provides the following embodiments of Method 1:

1.1 Method 1, further comprising the step of:
   ii) administering the composition to the individual;
      whereby the administration of the composition results in either:
      a) the clearance of alcohol from the body at a faster rate than clearance associated with, or observed under normal physiology; and/or
      b) the improvement of cognitive ability at a faster rate than improvement associated with, or observed under normal physiology.

1.2 Method 1, wherein the administration of the composition results in the clearance of alcohol from the body at a faster rate than clearance associated with, or observed under normal physiology.

1.3 Any preceding Method 1 or 1.1 et seq., wherein the clearance rate is determined by a standard breathalyzer machine.

1.4 Any preceding Method 1 or 1.1 et seq., wherein the composition is self-administered by the individual.

1.5 Any preceding Method 1 or 1.1 et seq., further comprising administering at least one blood alcohol detection test.

1.6 Method 1.5, wherein the blood alcohol detection test is administered prior to the administration of the composition to the individual.

1.7 Method 1.5, wherein the blood alcohol detection test is administered after the administration of the composition to the individual.

1.8 Method 1.5, wherein blood alcohol detection tests are administered both before and after the administration of the composition to the individual.

1.9 Any preceding Method 1 or 1.1 et seq., further comprising the step of identifying the individual as an individual in need of reducing blood alcohol concentration.

1.10 Any preceding Method 1 or 1.1 et seq., wherein the individual is suffering from or is suspected of suffering from cognitive impairment due to alcohol.

1.11 Any preceding Method 1 or 1.1 et seq., further comprising the step of identifying the individual as an individual in need of improving cognitive ability.

In a further aspect, the present disclosure provides a Method [Method 2] for improving cognitive ability in an individual in need thereof who is suffering from or is suspected of suffering from cognitive impairment due to alcohol, comprising:
i) providing to the individual a composition according to any of Compositions 1 and 1.1 et seq., and/or Compositions 2 and 2.1 et seq.

The present disclosure further provides the following embodiments of Method 2:

2.1 Method 2, further comprising the step of:
ii) administering the composition to the individual;
whereby the administration of the composition results in the improvement of cognitive ability at a faster rate than improvement associated with, or observed under normal physiology.

2.2 Method 2 or 2.1, further comprising the step of identifying the individual as an individual in need of improving cognitive ability.

2.3 Method 2.2, wherein the individual is identified as being in need of improving cognitive ability due to cognitive impairment due to alcohol.

2.4 Any preceding Method 2 or 2.1 et seq., wherein the individual is suffering from or is suspected of suffering from cognitive impairment due to alcohol.

2.5 Any preceding Method 2 or 2.1 et seq., wherein the improving cognitive ability is determined by a Trail Making Test; the Montreal cognitive assessment (MoCA), Mini-mental state exam (MMSE), or the Mini-Cog test.

Alcohol is eliminated from the body by excretion and metabolism, typically through elimination by the kidney (urine), lung (exhale), or liver where it is chemically broken down to acetic acid. An average person can eliminate 0.5 oz (15 ml) of alcohol per hour. So, it would take approximately one hour to eliminate the alcohol from a 12 oz (355 ml) can of beer. Most alcohol is metabolized, or burned, in a manner similar to food, yielding carbon dioxide and water. A small portion of alcohol is excreted, such as through the breath, leaving the body as alcohol, unchanged. Elimination occurs at a constant rate for a given individual. The median rate of decrease in BAC is considered to be 15 milligrams percent (mg %) per hour. The range of decrease in BAC is 10-20 mg % per hour. This range represents the extreme ends of the rate encountered in a normal population. Most people eliminate at a rate of between 13 and 18 mg % per hour.

The administration of the Compositions of the present disclosure to an individual having elevated BAC results in clearance of alcohol from the body at a faster rate than clearance associated with, or observed, under normal physiological conditions; for example as measured by a standard breathalyzer machine.

As used herein, the term "clearance of alcohol from the body at a faster rate than clearance associated with normal physiological conditions" is intended go mean clearance at a rate that exceeds between 13 and 18 mg % per hour, more preferably exceeds 10-20 mg % per hour. As used herein, the term "clearance of alcohol from the body at a faster rate than clearance observed under normal physiological conditions" is intended go mean clearance at a rate that exceeds the individual's rate of clearance in the absence of the administration of the composition of the present disclosure.

In some embodiments, the present compositions may also be of benefit persons not suffering from alcohol intoxication; for example by potentially increasing mental acuity. Thus, in a further aspect, the present disclosure provides a Method [Method 3] for improving cognitive ability (and/or mental acuity) in an individual not suffering from alcohol intoxication, comprising:
i) providing to the individual a composition according to any of Compositions 1 and 1.1 et seq., and/or Compositions 2 and 2.1 et seq.

The present disclosure further provides the following embodiments of Method 3:

3.1 Method 3, further comprising the step of:
ii) administering the composition to the individual;
whereby the administration of the composition results in the improvement of cognitive ability and/or mental acuity.

In some embodiments, the present compositions may also reduce, alleviate, and/or ameliorate the severity of symptoms associated with alcohol intoxication (e.g., symptoms associated with "hangover"), including for example and not limitation, headache, nausea and fatigue. The present compositions may also improve general feeling of well-being that may be impaired subsequent to alcohol intoxication. Accordingly, in a further aspect, the present disclosure provides a Method [Method 4] for reducing, alleviating or ameliorating the severity of symptoms associated with alcohol intoxication (e.g., symptoms associated with "hangover"), including for example and not limitation, headache, nausea and fatigue, comprising:
i) providing to the individual a composition according to any of Compositions 1 and 1.1 et seq., and/or Compositions 2 and 2.1 et seq.

The present disclosure further provides the following embodiments of Method 4:

4.1 Method 4, further comprising the step of:
ii) administering the composition to the individual;
whereby the administration of the composition results in the reducing, alleviating or ameliorating the severity of symptoms associated with alcohol intoxication.

In some embodiments, a cognitive test is administered to an individual before or after administration of a composition of the present disclosure. The test can be any that is recognized to determine level of cognition. Examples include the Trail Making Test; the Montreal cognitive assessment (MoCA), Mini-mental state exam (MMSE), or the Mini-Cog test.

The Trail Making Test is a neuropsychological test of visual attention and task switching. It has two parts, in which the subject is instructed to connect a set of 25 dots as quickly as possible while maintaining accuracy. The test can provide information about visual search speed, scanning, speed of processing, mental flexibility, and executive functioning.

The Montreal cognitive assessment (MoCA) is a short test that lasts around 15 minutes. It involves memorizing a short list, categorizing images in pictures, and copying shapes. This test is the best for finding mild cognitive impairment. The Mini-mental state exam (MMSE) lasts around 10 minutes, and involves saying the date and other common, well-known facts, counting backward, and identifying objects in the room. The Mini-Cog test involves memorizing and recalling a three-word list of unrelated words and drawing a circle clock-adding all time points, then drawing hands to show a specific time.

In some embodiments, the composition comprises theacrine, also known as 1,3,7,9-tetramethyluric acid, which is a purine alkaloid found in Cupuaçu and in a Chinese tea known as kucha. Some studies suggest it may have beneficial qualities, such as serving as an effective anti-oxidant, anti-inflammatory and may have anti-obesity properties.

In some embodiments, the composition comprises methylliberine (e.g. Dynamine®), a methoxyuric acid, which is a caffeine metabolite present at low levels in various Coffee plants. There is continuous interest in methylliberine as an ingredient in functional foods and dietary supplements. Based on its structural similarity to caffeine and theacrine, methylliberine is widely believed to be an adenosine receptor antagonist.

In some embodiments, the composition comprises Theobromine, also known as xantheose, which is the principal alkaloid of the cacao bean.

In some embodiments, the composition comprises Citicoline, also known as cytidine diphosphate-choline or cytidine 5'-diphosphocholine is an intermediate in the generation of phosphatidylcholine from choline, a common biochemical process in cell membranes. It has been experimentally proven that CDP-choline increases noradrenaline and dopamine levels in the CNS. Due to these pharmacological activities, CDP-choline has a neuroprotective effect in situations of hypoxia and ischemia, as well as improved learning and memory performance in animal models of brain aging. See Methods Find. Exp. Clin. Pharmacol. 1995 October: 17 Suppl B: 1-54.

In some embodiments, the composition comprises synephrine, which is an alkaloid, and one of the tyramine metabolite components of Bitter Orange, which act on the $\alpha_1$-adrenergic receptor to constrict blood vessels and increase blood pressure and heart rate.

In some embodiments, the composition comprises *Macuna pruriens*, which has a wide range of therapeutic qualities, including antidiabetics, antiinflammation, analgesia, neuroprotection, arousal, and antioxidant. This plant's high alkaloid content makes it an attractive first-line therapy for Parkinson Disease in Ayurvedic medicine. See Mihir Kumar Purkait, Dibyajyoti Haldar and Prangan Duarah, Advances in Extraction and Applications of Bioactive Phytochemicals (2023) Elsevier Inc.

In some embodiments, the composition comprises N-acetyl L-cysteine (NAC). It is a pharmaceutical drug and nutritional supplement which has been used primarily as a mucolytic agent (expectorant), and in the management of paracetamol (acetaminophen) overdose. Other uses include sulfate repletion in conditions, such as autism, where cysteine and related sulfur amino acids may be depleted. NAC is a derivative of cysteine in which an acetyl group is attached to the nitrogen atom. It is sold as a dietary supplement commonly claiming antioxidant and liver protecting effects (detoxifying). It is used as a cough medicine because it breaks disulfide bonds in mucus and liquefies it, making it easier to cough up. It is also this action of breaking disulfide bonds that makes it useful in thinning the abnormally thick mucus in Cystic Fibrosis patients.

In some embodiments, the composition comprises milk thistle, which is a plant named for the white veins on its large prickly leaves. One of the active ingredients in milk thistle called silymarin is extracted from the plant's seeds and is believed to have antioxidant properties. It is used as a supplement to treat liver conditions, and research on milk thistle use for specific conditions shows potential benefits for diabetes, indigestion (dyspepsia) and liver disease.

In some embodiments, the composition comprises *ginseng*, for example Korean Red *Ginseng* (aka *Panax ginseng*/ Asian *Ginseng*) and/or derivations thereof that include extracted ginsenosides). *Ginseng* (*Panax ginseng* CAM-eyer) is a plant belonging to the genus *Ginseng* of the family Ukogi and is a herbal medicine used for about 2,000 years in Korea, China, Japan, etc. It is used for the purpose of extending the life span. Until now, *ginseng* has the following effects and effects: positive effects on central nervous system, anti-carcinogenic activity, anti-cancer activity, immune function modulation effect, anti-diabetic activity, liver function enhancing efficacy, improvement of cardiovascular disease, anti-arterial It has been found that it has a hardening effect, blood pressure control action, improvement of menopausal disorders, improvement of osteoporosis, anti-stress and anti-fatigue action, antioxidant activity and anti-aging effect etc. See Latest *ginseng* "component and efficacy", Korea *Ginseng* Tobacco Research Institute, 56-112, 1996.

In some embodiments, the composition comprises N-acetyl tyrosine, which is an acetylated derivative of the amino acid L-tyrosine, which is the precursor of neurotransmitters dopamine (DA) and norepinephrine (NE). N-acetyl Tyrosine is thought to support memory and thinking skills (cognitive function) by supporting the synthesis of the catecholamines norepinephrine and dopamine (neurotransmitters), and to replenish catecholamine levels in the brain, which can become depleted under stressful conditions.

In some embodiments, the composition comprises taurine, or 2-aminoethanesulfonic acid, which is a non-proteinogenic amino sulfonic acid that is widely distributed in animal tissues. It is a major constituent of bile and can be found in the large intestine, and accounts for up to 0.1% of total human body weight. Taurine has important functions in the heart and brain, where it is thought to help support nerve growth.

In some embodiments, the composition comprises cocoa extract, which is a mixture with a chocolate taste, made up of xanthine molecules (theobromine and caffeine) and procyanidins. Supplements with cocoa extract have been proposed to provide cardiovascular and cognitive benefits through improved blood flow and antioxidant effects.

In some embodiments, the composition comprises phenylalanine, which is a non-essential amino acid. It has been used for a disorder that causes white patches to develop on the skin (vitiligo), and for attention-deficit hyperactivity disorder (ADHD), chronic pain, aging skin, depression and other purposes.

In some embodiments, the present composition comprises dandelion extract. Dandelion is extracted for its diuretic, anti-inflammatory, antioxidant properties, liver and digestive support. Dandelion extract (for example but not limitation dandelion leaf extract) is typically prepared by drying, seeping in a solvent, filtering and then drying.

In some embodiments, the present composition comprises apple extract (e.g., apple pectin). Apple pectin/extract can be prepared from various apple species and has been shown to improve gastrointestinal health, inflammation, cardiovascular health, immune support and detoxification. Apple pectin/ extract is typically prepared by boiling the apples down until the pectin is released, and then the material is filtered and dried. In some embodiments, a bend of apples is employed.

In some embodiments, the composition comprises Huperzine A, a naturally-occurring sesquiterpene alkaloid compound found in the firmoss *Huperzia serrata*, and in varying quantities in other food *Huperzia* species, including *H. elmeri, H. carinat,* and *H. aqualupian.* Huperzine A inhibits the breakdown of the neurotransmitter acetylcholine (ACh) by the enzyme acetylcholinesterase. It used as a cognitive enhancer.

In some embodiments, the composition comprises Quercetin, which belongs to a group of plant pigments called flavonoids that give many fruits, flowers, and vegetables their colors. Flavonoids, such as quercetin, are antioxidants, that scavenge free radicals that can damage cell membranes and DNA.

In some embodiments, the composition comprises Hordenine, a chemical naturally found in barley (*Hordeum vulgare*). It can also be found in algae, cacti, and some grass species. It is similar in chemical structure to stimulants found in bitter orange, and included in many dietary supplements used for athletic performance and weight loss. Hordenine has also been proposed to use for use in obesity, and improving athletic performance.

In some embodiments, the composition comprises *Eria jarensis*, which is a dietary supplement derived from an orchid plant native to Southeast Asia. It is used to boost energy levels, improve mood, and reduce stress. It is also believed to have cognitive-enhancing properties.

In some embodiments, the composition comprises glycine, an amino acid that contributes to cellular growth and health. Glycine is one of the amino acids essential to the body's synthesis of the antioxidant glutathione. Cells produce glutathione to scavenge free radicals that can otherwise cause oxidative stress and damage cells, proteins, and DNA. It is thought that through supplementation with glycine and cysteine the body can restore age-related loss of the ability to naturally synthesize glutathione. Glycine also plays a role in the synthesis of creatine, another amino acid that can also be consumed independently, which provides muscles with the energy needed for short bursts of strength and speed, and also provides the brain energy, and possibly can help with cognitive tasks such as short-term memory and reasoning.

In some embodiments, the composition comprises betaine, also called betaine anhydrous, or trimethylglycine (TMG). Betaine is involved in liver function, cellular reproduction, and helping make carnitine. It also helps the body metabolize homocysteine, and has been approved by the FDA to treat a genetic condition where too much homocysteine builds up in the body. Studies also suggest that betaine, along with vitamins B6, B12, and folic acid, helps reduce higher levels of homocysteine, and that high levels of homocysteine may encourage atherosclerosis (hardening of the arteries). Studies in rats suggest that betaine may help protect against harmful fatty deposits in the liver. These deposits can be caused by alcohol abuse, obesity, diabetes, and other causes. Preliminary studies in people have shown similar results. Betaine is also thought to be of possible use relief of dry mouth, and in prophylaxis of lung cancer by minimizing the adverse effects of smoking, and possibly lowering the risk of breast cancer.

In some embodiments, the composition comprises alpha lipoic acid, an antioxidant that is made naturally in the body and also found in foods. It is used to break down carbohydrates and to make energy. Because alpha-lipoic acid seems to work like an antioxidant, it might provide protection to the brain and also be helpful in certain liver diseases. Alpha-lipoic acid has also been proposed for use for nerve pain in people with diabetes, and for obesity, altitude sickness, aging skin, high levels of cholesterol or other fats in the blood, and many other purposes.

In some embodiments, the composition comprises palmitoylethanolamide (PEA), which is an endogenous fatty acid amide, and lipid modulator. There is evidence that it binds to a nuclear receptor, through which it exerts a variety of biological effects, some related to chronic inflammation and pain. PEA is used for different types of pain, fibromyalgia, osteoarthritis, multiple sclerosis (MS), carpal tunnel syndrome, autism, and many other conditions, In some embodiments, the composition comprises Tumeric, which has been studied in numerous clinical trials for various human diseases and conditions.

In some embodiments, the composition comprises glutathione, which is an antioxidant that plays numerous important roles in chemical reactions in the body. Glutathione is capable of preventing damage to important cellular components caused by sources such as reactive oxygen species, free radicals, peroxides, lipid peroxides and heavy metals.

Other useful components include Probiotics (e.g., *Lactobacillus* and *Bifidobacterium*), Japanese Mountain Ash (*Sorbus commixta*), Japanese Alder (*Alnus japonica*), Asian Hazel (*Corylus heterophylla*), artichoke extract, and yellow dock root (*Rumex crispus*), ginger. licorice, chitosan and inulin.

The Compositions of the present disclosure may be prepared in ways known to be useful to those of ordinary skill in the art of preparing solutions and suspensions for oral consumption.

EXAMPLES

Example 1-BACtrack® S80 Breathalyzer Determination of Reduction of BAC Levels in Individuals with Elevated BAC A drink was prepared including (mg dry powder weight per single serving; e.g., per 12-oz can):

| | |
|---|---|
| Theacrine | 50.00 |
| Methyliberine | 75.00 |
| Phenylalanine | 200.00 |
| Theobromine | 200.00 |
| Caffeine | 225.00 |
| N-Acetyl Tyrosine | 500.00 |
| Taurine | 500.00 |
| Glycine | 350.00 |
| Synephrine 98% | 80.00 |
| Macuna Pruriens 98% | 250.00 |
| Cognizin (cdp choline) | 250.00 |
| Apple Pectin Extract | 2000.00 |
| Huperzine A 1% | 50.00 |
| Dandelion Leaf Extract (4:1) | 500.00 |
| N-Acetyl Cysteine | 1000.00 |
| Panax Ginseng Root 5% | 150.00 |
| Milk Thistle (80% Silymarin) | 400.00 |
| B12 (Methyl cobalamin) | 0.06 |
| P5P (B6) | 2.50 |
| Pyridoxine HCL (B6) | 2.50 |
| B1 (Thiamine) | 4.00 |
| B2 (Riboflavin) | 4.00 |
| B3 (Niacin) | 32.00 |
| B5 (Pantothenic Acid) | 35.00 |
| Calcium Citrate | 250.00 |

-continued

| | |
|---|---|
| Sodium Citrate | 500.00 |
| Potassium Chloride | 125.00 |
| Magnesium Citrate | 250.00 |

This drink was then given to 10 individuals who's breath have registered about 0.09 to about 0.20 on a BACtrack® S80 breathalyzer. After 30-45 minutes the same individuals were tested again. It is expected that alcohol would continue to be absorbed during this time but each person tested showed significant reduction in the breathalyzer reading. Typical of the results expected were: 0.09 lowered to 0.06; 0.13 lowered to 0.09; and 0.20 lowered to 0.13.

Example 2-BACtrack® S80 Breathalyzer Determination of Reduction of BAC Levels in Individuals with Elevated BAC A drink is prepared including (as mg/serving) the following active ingredients:

| | |
|---|---|
| Theacrine | 50.00 |
| Methyliberine | 75.00 |
| Phenylalanine | 200.00 |
| Theobromine | 200.00 |
| Caffeine | 225.00 |
| N-Acetyl Tyrosine | 500.00 |
| Taurine | 500.00 |
| Glycine | 350.00 |
| Synephrine 98% | 80.00 |
| Macuna Pruriens 98% | 250.00 |
| Cognizin (cdp choline) | 250.00 |
| Apple Pectin Extract | 2000.00 |
| Huperzine A 1% | 50.00 |
| Dandelion Leaf Extract (4:1) | 500.00 |
| N-Acetyl Cysteine | 1000.00 |
| Panax Ginseng Root 5% | 150.00 |
| Milk Thistle (80% Silymarin) | 400.00 |

This drink is then given to 10 individuals who's breath register about 0.09 to about 0.20 on a BACtrack® S80 breathalyzer. After 30-45 minutes the same individuals are tested again. It is expected that alcohol will continue to be absorbed during this time, and it is expected that each person tested will show a significant reduction in the breathalyzer reading, for example a BAC of 0.09 lowering to 0.06; a BAC of 0.13 lowering to 0.09; and a BAC of 0.20 lowering to 0.13.

Example 3-BACtrack® S80 Breathalyzer Determination of Reduction of BAC Levels in Individuals with Elevated BAC A drink is prepared including (as mg/serving) the following active ingredients:

| | |
|---|---|
| Theacrine | 50.00 |
| Methyliberine | 75.00 |
| Phenylalanine | 200.00 |
| Theobromine | 200.00 |
| Caffeine | 225.00 |
| N-Acetyl Tyrosine | 500.00 |
| Taurine | 500.00 |
| Glycine | 350.00 |
| Synephrine 98% | 80.00 |
| Macuna Pruriens 98% | 250.00 |
| Cognizin (cdp choline) | 250.00 |
| Apple Pectin Extract | 2000.00 |
| Huperzine A 1% | 50.00 |
| Dandelion Leaf Extract (4:1) | 500.00 |
| N-Acetyl Cysteine | 1000.00 |
| Panax Ginseng Root 5% | 150.00 |
| Milk Thistle (80% Silymarin) | 400.00 | and one or more of the following:

| Component | Mg/serving |
|---|---|
| B Vitamin; e.g. one or more of B1 (Thiamine), B2 (Riboflavin), B3 (Niacin), B5 (Pantothenic Acid), B6 (pyridoxine; Pyridoxal 5 Phosphate and Pyridoxine HCL), B12 (methylcobalamin) | about 9 to about 171 |
| N-acetyl tyrosine | about 100 to about 1000 |
| Taurine | about 100 to about1000 |
| Cocoa extract | about 100 to about 1000 |
| Phenylalanine | about 50 to about 300 |
| Huperzine A | about 5 to about 100 |
| Magnesium citrate | about 50 to about 800 |
| Potassium chloride | about 25 to about 500 |
| Sodium citrate | about 100 to about 1500 |
| Calcium citrate | about 50 to about 1000 |
| Glycine | about 50 to about 500 |

This drink is then given to 10 individuals who's breath register about 0.09 to about 0.20 on a BACtrack® S80 breathalyzer. After 30-45 minutes the same individuals are tested again. It is expected that alcohol will continue to be absorbed during this time, and it is expected that each person tested will show a significant reduction in the breathalyzer reading, for example a BAC of 0.09 lowering to 0.06; a BAC of 0.13 lowering to 0.09; and a BAC of 0.20 lowering to 0.13.

Example 4-BACtrack® S80 Breathalyzer Determination of Reduction of BAC Levels in Individuals with Elevated BAC A drink was prepared including (as mg/serving) the following ingredients:

| Component | Mg/Serving |
|---|---|
| theacrine | about 5 to about 150 |
| methylliberine | about 5 to about 120 |
| theobromine | about 50 to about 250 |
| caffeine | about 50 to about 400 |
| cdp choline | about 25 to about 500 |
| synephrine (or synephrine HCl) | about 10 to about 150 |
| macuna pruriens | about 50 to about 500 |
| apple pectin | about 500 to about 3000 |
| dandelion extract | about 50 to about 1000 |
| N-acetyl cysteine | about 100 to about 1500 |
| *milk thistle | about 50 to about 600 |
| Ginseng, for example Korean Red Ginseng (aka Panax Ginseng/Asian Ginseng) and/or derivations thereof that include extracted ginsenosides | about 25 to about 400 |
| B Vitamin; e.g. one or more of B1 (Thiamine), B2 (Riboflavin), B3 (Niacin), B5 (Pantothenic Acid), B6 (pyridoxine; Pyridoxal 5 Phosphate and Pyridoxine HCL), B12 (methylcobalamin) | about 9 to about 171 |

-continued

| Component | Mg/Serving |
|---|---|
| N-acetyl tyrosine | about 100 to about 1000 |
| Taurine | about 100 to about 1000 |
| Phenylalanine | about 50 to about 300 |
| Huperzine A | about 5 to about 100 |
| Magnesium citrate | about 50 to about 800 |
| Potassium chloride | about 25 to about 500 |
| Sodium citrate | about 100 to about 1500 |
| Calcium citrate | about 50 to about 1000 |
| Citric acid | about 50 to about 1500 |
| Glycine | about 50 to about 500 |
| Potassium sorbate | about 80 to about 200 |
| Sodium benzoate | about 80 to about 200 |
| Sucralose | about 350 to about 450 |

This drink was then given to 10 individuals who's breath registered about 0.09 to about 0.20 on a BACtrack® S80 breathalyzer. After 30-45 minutes the same individuals were tested again. It is expected that alcohol will continue to be absorbed during this time, and it was found that each person tested showed a significant reduction in the breathalyzer reading, generally of the same magnitude as described above in Example 1.

While the invention has been described in connection with what is presently considered to be the most practical and preferred embodiment, it is to be understood that the invention is not to be limited to the disclosed embodiments, but to the contrary, it is intended to cover various modifications or equivalent arrangements included within the spirit and scope of the appended claims. The scope is to be accorded the broadest interpretation so as to encompass all such modifications and equivalent structures as is permitted under the law.

Each of the patents, books, articles and other printed publications referenced herein are incorporated by reference in their entireties for all purposes.

What is claimed is:

1. A composition for reducing blood alcohol concentrations (BAC) in an individual impaired or suspected of being impaired by alcohol comprising an effective amount of:
   theacrine;
   methylliberine;
   theobromine;
   caffeine;
   cdp choline;
   synephrine;
   *Macuna pruriens;*
   apple pectin;
   dandelion extract;
   n-acetyl cysteine;
   milk thistle; and
   *Ginseng,* and/or derivations thereof; wherein said derivations include extracted ginsenosides;
   whereby the administration of the composition to the individual results in clearance of alcohol from the body at a faster rate than clearance associated with, or observed, under normal physiological conditions as measured by a standard breathalyzer machine.

2. The composition of claim 1 wherein the components are present in the following amounts:

| Component | Mg/serving |
|---|---|
| theacrine | about 5 to about 150 |
| methylliberine | about 5 to about 120 |
| theobromine | about 50 to about 250 |
| caffeine | about 50 to about 400 |
| cdp choline | about 25 to about 500 |
| synephrine or synephrine HCl | about 10 to about 150 |
| macuna pruriens | about 50 to about 500 |
| apple pectin | about 500 to about 3000 |
| dandelion extract | about 50 to about 1000 |
| N-acetyl cysteine | about 100 to about 1500 |
| milk thistle | about 50 to about 600 |
| Ginseng and/or derivations thereof; wherein said derivations include extracted ginsenosides | about 25 to about 400. |

3. The composition of claim 1 further comprising one or more of: a B vitamin; N-acetyl tyrosine; taurine; cocoa extract; phenylalanine; Huperzine A; magnesium citrate; sodium citrate; calcium citrate; potassium chloride and/or glycine.

4. The composition of claim 2, further comprising the following components in the following amounts:

| Component | Mg/serving |
|---|---|
| One or more B Vitamins selected from B1, B2, B3, B5, B6, and B12 | about 9 to about 171 |
| N-acetyl tyrosine | about 100 to about 1000 |
| Taurine | about 100 to about 1000 |
| Cocoa extract | about 100 to about 1000 |
| Phenylalanine | about 50 to about 300 |
| Huperzine A | about 5 to about 100 |
| Magnesium citrate | about 50 to about 800 |
| Potassium chloride | about 25 to about 500 |
| Sodium citrate | about 100 to about 1500 |
| Calcium citrate | about 50 to about 1000 |
| Citric acid | about 50 to about 1500 |
| Glycine | about 50 to about 500. |

5. The composition of claim 1, further comprising one or more of betaine, quercetin, hordenine, palmitoylethanolamide, artichoke extract, yellow dock root, turmeric, glutathione, ginger, licorice, chitosan, inulin, and combinations thereof.

6. The composition of claim 1 further comprising water wherein the water is present at a concentration of from about 80 weight percent to 99 weight percent.

7. The composition according to claim 1, comprising the following components:

Component
theacrine
methylliberine
theobromine
caffeine
cdp choline
synephrine or synephrine HCl
macuna pruriens
apple pectin
dandelion extract
N-acetyl cysteine
milk thistle
Ginseng and/or derivations thereof; wherein said derivations include extracted ginsenosides
One or more B Vitamins selected from Vitamins B1, B2, B5, B6 and B12

N-acetyl tyrosine
Taurine
Phenylalanine
Huperzine A
Magnesium citrate
Potassium chloride
Sodium citrate
Calcium citrate
Citric acid
Glycine.

8. The composition according to claim 1, comprising the following components in the following amounts:

| Component | Mg/Serving |
| --- | --- |
| theacrine | about 5 to about 150 |
| methylliberine | about 5 to about 120 |
| theobromine | about 50 to about 250 |
| caffeine | about 50 to about 400 |
| cdp choline | about 25 to about 500 |
| synephrine or synephrine HCl | about 10 to about 150 |
| macuna pruriens | about 50 to about 500 |
| apple pectin | about 500 to about 3000 |
| dandelion extract | about 50 to about 1000 |
| N-acetyl cysteine | about 100 to about 1500 |
| milk thistle | about 50 to about 600 |
| Ginseng, and/or derivations thereof; wherein said derivations include extracted ginsenosides | about 25 to about 400 |
| One or more B Vitamins selected from Vitamins B1, B2, B5, B6 and B12 | about 9 to about 171 |
| N-acetyl tyrosine | about 100 to about 1000 |
| Taurine | about 100 to about 1000 |
| Phenylalanine | about 50 to about 300 |
| Huperzine A | about 5 to about 100 |
| Magnesium citrate | about 50 to about 800 |
| Potassium chloride | about 25 to about 500 |
| Sodium citrate | about 100 to about 1500 |
| Calcium citrate | about 50 to about 1000 |
| Citric acid | about 50 to about 1500 |
| Glycine | about 50 to about 500. |

9. The composition according to claim 8, further comprising one or more preservatives, sweeteners and/or natural flavors.

10. The composition according to claim 9, wherein the preservatives are selected from sorbate and benzoate salts; and the sweeteners are selected from sucralose, mannitol, sorbitol, xylitol, *stevia*, saccharin sodium, fructose, high fructose corn syrup, maltodextrin, sucrose and monk fruit.

11. A composition for reducing blood alcohol concentrations (BAC) in an individual impaired or suspected of being impaired by an alcohol comprising the following ingredients:
Theacrine
Methyliberine
Phenylalanine
Theobromine
Caffeine
N-Acetyl Tyrosine
Taurine
Glycine
Synephrine with 98% purity
*Macuna pruriens* with 98% purity
cdp choline
Apple Pectin Extract
Huperzine A with 1% purity
Dandelion Leaf Extract (4:1)
N-Acetyl Cysteine
*Panax ginseng* Root with 5% purity
Milk Thistle comprising (80% Silymarin
Vitamin B12
Pyridoxal 5'-phosphate (P5P)
Pyridoxine HCl
Vitamin B1
Vitamin B2
Vitamin B3
Vitamin B5
Calcium Citrate
Sodium Citrate
Potassium Chloride and
Magnesium Citrate;
whereby the administration of the composition to the individual results in clearance of alcohol from the body at a faster rate than clearance associated with, or observed, under normal physiological conditions as measured by a standard breathalyzer machine.

12. The composition of claim 11 wherein the components are present at +/− about 25% of the following amounts:

| Theacrine | 50 mg/serving |
| --- | --- |
| Methyliberine | 75 mg/serving |
| Phenylalanine | 200 mg/serving |
| Theobromine | 200 mg/serving |
| Caffeine | 225 mg/serving |
| N-Acetyl Tyrosine | 500 mg/serving |
| Taurine | 500 mg/serving |
| Glycine | 350 mg/serving |
| Synephrine with 98% purity | 80 mg/serving |
| Macuna Pruriens with 98% purity | 250 mg/serving |
| cdp choline | 250 mg/serving |
| Apple Pectin Extract | 2000 mg/serving |
| Huperzine A with 1% purity | 50 mg/serving |
| Dandelion Leaf Extract (4:1) | 500 mg/serving |
| N-Acetyl Cysteine | 1000 mg/serving |
| Panax Ginseng Root with 5% purity | 150 mg/serving |
| Milk Thistle comprising 80% Silymarin | 400 mg/serving |
| Vitamin B12 | 0.06 mg/serving |
| P5P | 2.5 mg/serving |
| Pyridoxine HCl | 2.5 mg/serving |
| Vitamin B1 | 4 mg/serving |
| Vitamin B2 | 4 mg/serving |
| Vitamin B3 | 32 mg/serving |
| Vitamin B5 | 35 mg/serving |
| Calcium Citrate | 250 mg/serving |
| Sodium Citrate | 500 mg/serving |
| Potassium Chloride | 125 mg/serving |
| Magnesium Citrate | 250 mg/serving. |

13. The composition of claim 1, wherein alcohol is cleared from the body at a faster rate that is at least 10% faster; or at least 15% faster; or at least 20% faster; or at least 25% faster; or at least 30% faster than clearance associated with, or observed, under normal physiological conditions.

14. The composition of claim 1, wherein the BAC of the individual is decreased by greater than 20 mg % per hour; or greater than 21 mg % per hour; or greater than 22 mg % per hour; or greater than 23 mg % per hour; or greater than 24 mg % per hour; or greater than 25 mg % per hour; after administration of the composition.

15. The composition of claim 1, wherein the composition is a liquid for oral administration.

16. The composition of claim 1, wherein the composition is in the form of a tablet, capsule, caplet, pill, gel cap, dry powder, liquid, or suspension.

17. A method for improving cognitive ability and/or reducing blood alcohol concentrations in an individual in need thereof who is suffering from or is suspected of suffering from cognitive impairment due to alcohol, the method comprising: i) providing to the individual a composition according to claim 7.

18. The method of claim 17, further comprising the step of:
ii) administering the composition to the individual;
whereby the administration of the composition results in either:
a) the clearance of alcohol from the body at a faster rate than clearance associated with or observed under, normal physiology; or
b) the improvement of cognitive ability at a faster rate than improvement associated with or observed under, normal physiology.

19. The method of claim 18, wherein the composition is self-administered by the individual.

20. The method of claim 18, further comprising administering at least one blood alcohol detection test.

21. The method of claim 20 wherein the blood alcohol detection test is administered prior to the administration of the composition to the individual, or after the administration of the composition to the individual.

22. The method of claim 20 wherein blood alcohol detection tests are administered both before and after the administration of the composition to the individual.

23. The method of claim 17, further comprising the step of identifying the individual as an individual in need of reducing blood alcohol concentration.

24. The method of claim 17, further comprising the step of identifying the individual as an individual in need of improving cognitive ability.

25. The composition of claim 7, wherein alcohol is cleared from the body at a faster rate that is at least 10% faster; or at least 15% faster; or at least 20% faster; or at least 25% faster; or at least 30% faster than clearance associated with, or observed, under normal physiological conditions.

26. The composition of claim 7, wherein the BAC of the individual is decreased by greater than 20 mg % per hour; or greater than 21 mg % per hour; or greater than 22 mg % per hour; or greater than 23 mg % per hour; or greater than 24 mg % per hour; or greater than 25 mg % per hour; after administration of the composition.

27. The composition of claim 7, wherein the composition is a liquid for oral administration.

28. The composition of claim 7, wherein the composition is in the form of a tablet, capsule, caplet, pill, gel cap, dry powder, liquid, or suspension.

29. The composition of claim 27 further comprising water wherein the water is present at a concentration of from about 80 weight percent to 99 weight percent.

* * * * *